(12) United States Patent
Iso et al.

(10) Patent No.: US 11,719,627 B2
(45) Date of Patent: Aug. 8, 2023

(54) CALIBRATION CURVE SETTING METHOD USED FOR DRUG ANALYSIS

(71) Applicant: HORIBA, LTD., Kyoto (JP)

(72) Inventors: Eishi Iso, Kyoto (JP); Shinsuke Kashiwagi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 1113 days.

(21) Appl. No.: 16/419,424

(22) Filed: May 22, 2019

(65) Prior Publication Data

US 2019/0369010 A1 Dec. 5, 2019

(30) Foreign Application Priority Data

May 29, 2018 (JP) ................. 2018-102139

(51) Int. Cl.
*G01N 21/27* (2006.01)
*G01N 21/65* (2006.01)
(Continued)

(52) U.S. Cl.
CPC .......... *G01N 21/274* (2013.01); *G01N 21/65* (2013.01); *G01N 33/15* (2013.01); *G01D 5/347* (2013.01);
(Continued)

(58) Field of Classification Search
CPC ............... G01N 21/65; G01N 21/274; G01N 2021/3133; G01N 2021/655;
(Continued)

(56) References Cited

U.S. PATENT DOCUMENTS 8,359,164 B2 1/2013 Li
2011/0045598 A1 2/2011 Busch et al.
(Continued)

FOREIGN PATENT DOCUMENTS

EP 2302359 A1 3/2011
JP 2000-249654 A 9/2000
(Continued)

OTHER PUBLICATIONS

EPO, Office Action for the related European patent application No. 19176912.4, dated Feb. 11, 2022.
(Continued)

*Primary Examiner* — Hoa Q Pham
(74) *Attorney, Agent, or Firm* — Lucas & Mercanti, LLP (57) ABSTRACT

A calibration curve setting method used at the time of quantitatively analyzing specific components in a drug by a transmission Raman spectrum, the method comprising the steps of: obtaining respective transmission Raman spectra of a plurality of different wave number ranges including Raman bands corresponding to the specific components of a plurality of known drugs of which concentrations or amounts of the specific components are known and the concentrations or the amounts are different from each other; calculating candidate calibration curves which are candidates for calibration curves used for the quantitative analysis respectively from a plurality of transmission. Raman spectra in each of the wave number ranges; and using the most probable candidate calibration curve as a calibration curve for the quantitative analysis of the specific components, among the respective candidate calibration curves.

6 Claims, 6 Drawing Sheets

(51) Int. Cl.
*G01N 33/15* (2006.01)
*G01D 5/347* (2006.01)
*G01N 21/31* (2006.01)
*G06F 17/18* (2006.01)

(52) U.S. Cl.
CPC ............... *G01N 2021/3133* (2013.01); *G01N 2201/12761* (2013.01); *G06F 17/18* (2013.01)

(58) Field of Classification Search
CPC . G01N 2201/1293; G01N 2201/12761; G01N 33/15; A61B 5/0075
USPC .......................................... 356/301–326, 417
See application file for complete search history.

(56) References Cited

U.S. PATENT DOCUMENTS

| | | |
|---|---|---|
| 2012/0092663 A1 | 4/2012 | Kull et al. |
| 2012/0176603 A1* | 7/2012 | Jung ...................... G01N 21/64 356/301 |
| 2013/0271758 A1 | 10/2013 | Marchant et al. |

FOREIGN PATENT DOCUMENTS

| | | |
|---|---|---|
| JP | 2009-244112 A | 10/2009 |
| JP | 2009-536317 A | 10/2009 |
| JP | 2014-149261 A | 8/2014 |
| JP | 2015-135323 A | 7/2015 |
| JP | 2015-529100 A | 10/2015 |
| WO | 2007/113566 A | 10/2007 |
| WO | 2014/027967 A1 | 2/2014 |
| WO | 2014094039 A1 | 6/2014 |

OTHER PUBLICATIONS

Masahiro Watari et al., "Application of Near Infrared Spectroscopy and Chemometrics to On-Line Analysis for Polymer Process," Bunseki Kagaku, 2010, pp. 379-397, vol. 59, No. 5.

JPO, Office Action for the related Japanese patent application No. 2018-102139, dated Oct. 19, 2021, with English translation.

Zhi-Min Zhang et al., "An Intelligent Background-Correction Algorithm for Highly Fluorescent Samples in Raman Spectroscopy," Journal of Raman Spectroscopy, Oct. 9, 2009, pp. 659-669, vol. 41, No. 6.

EPO, Extended European Search Report for the corresponding European patent application No. 19 176 912.4, dated Sep. 25, 2019 (9 pages).

* cited by examiner

Partial Least Square (PLS) Regression Analysis : Partial Least Square Regression

OBTAINING MATRIX (REGRESSION VECTOR) TO BE Y=A*C+R BY CALCULATION.

R IS RESIDUAL (ERROR), IN PLS, CALCULATING NEW DIMENSION ADDED WITH VARIATION AMOUNT OF BOTH A AND Y (CLS & ILS), AND FROM DATA PLOT (SCORE) OF EACH SAMPLE IN ITS SPACE, CALCULATING MATRIX (REGRESSION VECTOR) FOR PREDICTING CONCENTRATION VALUE BY LEAST SQUARE METHOD.

HOWEVER, IT IS NECESSARY TO DESIGNATE DIMENSION NUMBER OF NEW SPACE USED FOR QUANTIFICATION MODEL.

Selection of PLS Dimension Number, Evaluation of Quantification Accuracy

CALIBRATION CURVE SETTING METHOD USED FOR DRUG ANALYSIS

CROSS REFERENCE TO RELATED APPLICATION

The present application claims priority of JP 2018-102139, filed May 29, 2018, the priority of this application is hereby claimed and this application is incorporated herein by reference.

TECHNICAL FIELD

The present invention relates to a method of setting a calibration curve used for quantitatively analyzing a specific component of a drug such as a pharmaceutical, medicament and the like, based on transmission Raman light generated at the time of irradiating the drug with inspection light.

BACKGROUND ART

In recent years, in a pharmaceutical production process, there has been increasing a demand for performing a process monitoring procedure by a nondestructive and rapid analysis method to improve productivity.

On the other hand, in a technique of HPLC (high performance liquid chromatography) used in a process monitoring procedure in the conventional pharmaceutical production process, it is necessary to perform destructive analysis. Therefore, there is a drawback that a running cost becomes high and a long analysis time is required, and it is difficult to meet the aforementioned demand.

In addition, from a viewpoint that pharmaceuticals can be nondestructively analyzed, there has also been proposed a process monitoring procedure using a near-infrared absorption spectroscopy technique. However, in determination of effective components contained in pharmaceuticals, various different physical parameters (such as granule diameter and drug thickness) of the pharmaceuticals largely affect absorption spectrums, and broad absorption bands, that is a specific feature of the near-infrared absorption spectroscopy, overlap under affection of peaks due to multiple components. Therefore, it is difficult to obtain required qualitative accuracy and quantitative accuracy. In addition, although the analysis time is also a little short compared to that in HPLC, it is doubtful as to whether productivity of the pharmaceuticals can be sufficiently improved.

Meanwhile, as disclosed in, for example, Patent Literature 1, an example using a transmission Raman spectroscopy is known in component analysis of a pharmaceutical drug and the like.

According to this transmission Raman spectroscopy, a sharp peak can be obtained in a Raman spectrum, and since it has a high chemical discrimination ability, it is less subject to various different physical parameters (such as particle diameter and drug thickness). Furthermore, nondestructive analysis can be performed and analysis time is very short.

CITATION LIST

Patent Literatures

Patent Literature 1: Japanese Translation of PCT International Application Publication No. 2009-536317

SUMMARY OF INVENTION

Technical Problem

Therefore, the present invention has been made by focusing on transmission Raman spectroscopy, and a main object thereof is intended to further improve quantitative accuracy in drug analysis of pharmaceuticals and the like Without impairing advantages of the transmission Raman spectroscopy, that is, a point that nondestructive analysis is possible, a point that chemical discrimination ability is high, a point that analysis time is short, and a point that the whole drugs can be measured at once but not a local measurement.

Solution to Problem

That is, the present invention is directed to a calibration curve setting method that is used at the time of quantitatively analyzing specific components in a drug by a transmission Raman spectrum, the method includes the steps of:

obtaining respective transmission Raman spectra of a plurality of different wave number ranges including wave number components corresponding to the specific components of a plurality of known drugs of which concentrations or amounts of the specific components are known and the concentrations or the amounts are different from each other;

calculating candidate calibration curves which are candidates for calibration curves used for the quantitative analysis respectively from a plurality of transmission Raman spectra in each of the wave number ranges; and using the most probable candidate calibration curve as a calibration curve for the quantitative analysis of the specific components, among the respective candidate calibration curves.

According to the present invention having a configuration like this, the candidate calibration curves are calculated in each of the plurality of wave number ranges and the most probable one of them is selected as a calibration curve. Therefore, this results in that the calibration curve can be set using a transmission Raman spectrum close to the optimum wave number range for setting the calibration curve according to ambient conditions such as a kind of the specific component, a noise, background fluctuation, Raman peaks other than the specific component.

Therefore, the reliability of the calibration curve can be significantly improved, and the analysis accuracy can be consequently improved. Here, the "most probable" candidate calibration curve can include one having the smallest residual and one having the highest correlation coefficient.

As a specific embodiment, as each wave number range, there can be exemplified each wave number range that necessarily includes one peak wave number derived from the specific component in the transmission Raman spectrum and has a minimum range with a narrowest width and a maximum range with a widest width, and includes one or more intermediate ranges each having are intermediate width between the minimum range and the maximum range.

In order to further improve the accuracy of the quantitative analysis, it is preferable that, in the calculation of the candidate calibration curve, a predetermined pre-processing calculation is applied to a transmission Raman spectrum obtained directly from the drug and use a corrected transmission Raman spectrum and, multiple scattering corrections are applied in the pre-processing calculation.

More preferably, it is desirable to use regression analysis which is one of multivariate analysis for calculating the candidate calibration curve and to apply cross validation for setting the number of the components in the regression analysis.

Advantageous Effects of Invention

According to the present invention described above, the reliability of the calibration curve is significantly improved in the analysis of a drug using transmission Raman spectroscopy. In addition, the effect of the present invention can be obtained without impairing the merits of transmission Raman spectroscopy in drug analysis, that is, the point that the nondestructive analysis can be performed, the point that the chemical discrimination ability is high, and the point that the analysis time is short, and the like.

DESCRIPTION OF EMBODIMENTS

In the following, one embodiment of the present invention will be described with reference to the drawings.

Figure 1:
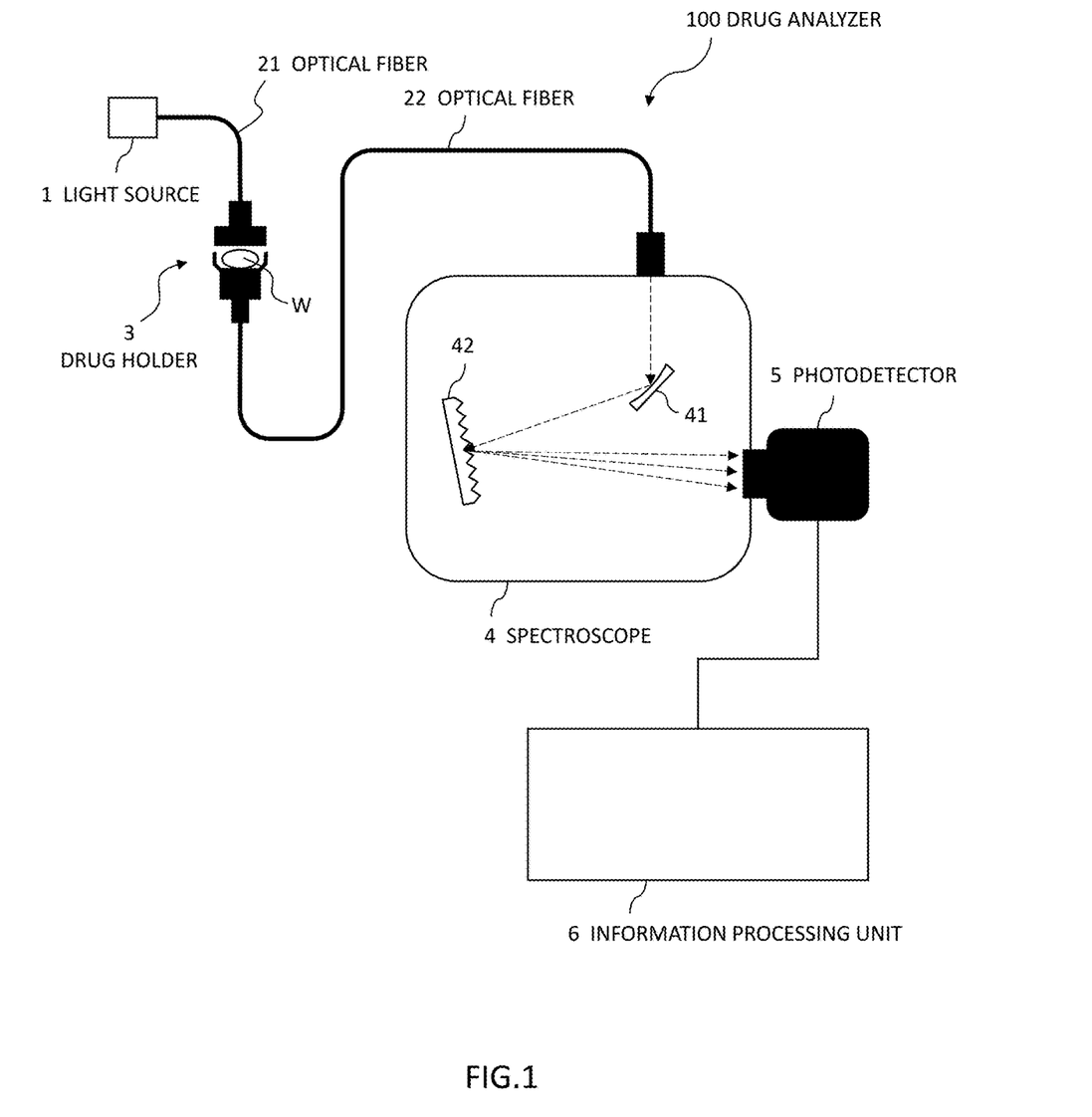
FIG. 1 is a schematic overall configuration diagram of a drug analyzer according to an embodiment of the present invention.

The drug analyzer 100 according to the present embodiment is intended to analyze and quantify a specific component contained in a drug W. As shown in FIG. 1, the drug analyzer 100 includes: a drug holder 3 for holding the drug W a light source 1 for irradiating the drug held by the drug holder 3 with near-infrared laser light as inspection light; a spectroscope 4 for spectrally dispersing transmission Raman light generated upon irradiation of the inspection light; a photodetector 5 for detecting intensity at each wavelength of the transmission Raman light spectrally dispersed by the spectroscope 4 and an information processing unit 6 for obtaining transmission Raman spectrum data from an output signal of the photodetector 5 and analyzing the data to calculate a concentration of the specific component. Note that, although a "drug" mentioned here is a pharmaceutical tablet (in addition to solidified powder, a thing in which liquid, powder, granules, etc. are filled in a capsule are also included), it is not limited to a tablet but unsolidified powders, granules, liquid and the like may be used, and not limited to a pharmaceutical but also agricultural chemicals, pesticides and the like may be used.

In this embodiment, the drug analyzer 100 is configured such that the inspection light emitted from the light source 1 is guided via a first optical fiber 21 to transmit substantially the entire part of the drug W from one side thereof and that the transmission Raman light generated upon irradiation of the inspection light is guided from the other side of the drug W to the spectroscope 4 via a second optical fiber 22.

Further, the spectroscope 4 includes; for example, a housing, one or more mirrors 41 disposed inside the housing; and a diffraction grating 42. Thus, the spectroscope 4 is configured such that, the transmission Raman light guided to the inside of the housing via the second optical fiber 22 is adjusted in its optical path by the mirror 41 and spectrally dispersed by the diffraction grating 42 and then guided to the photodetector 5 attached to the housing.

Then, the information processing unit 6 is an electronic device including a CPU, a memory an AD converter, and the like, and in this configuration, the CPU and its peripheral devices cooperate in accordance with a program stored in a predetermined area of the memory. Thus, the program causes the information processing unit 6 to function as a quantification unit (not shown) that performs quantitative analysis (in this case, quantitative determination of concentration) of one or more specific components contained in the drug and to function as a calibration curve setting unit 61 for setting a calibration curve used for quantitative determination performed by the quantification unit, and the like.

Figure 2:
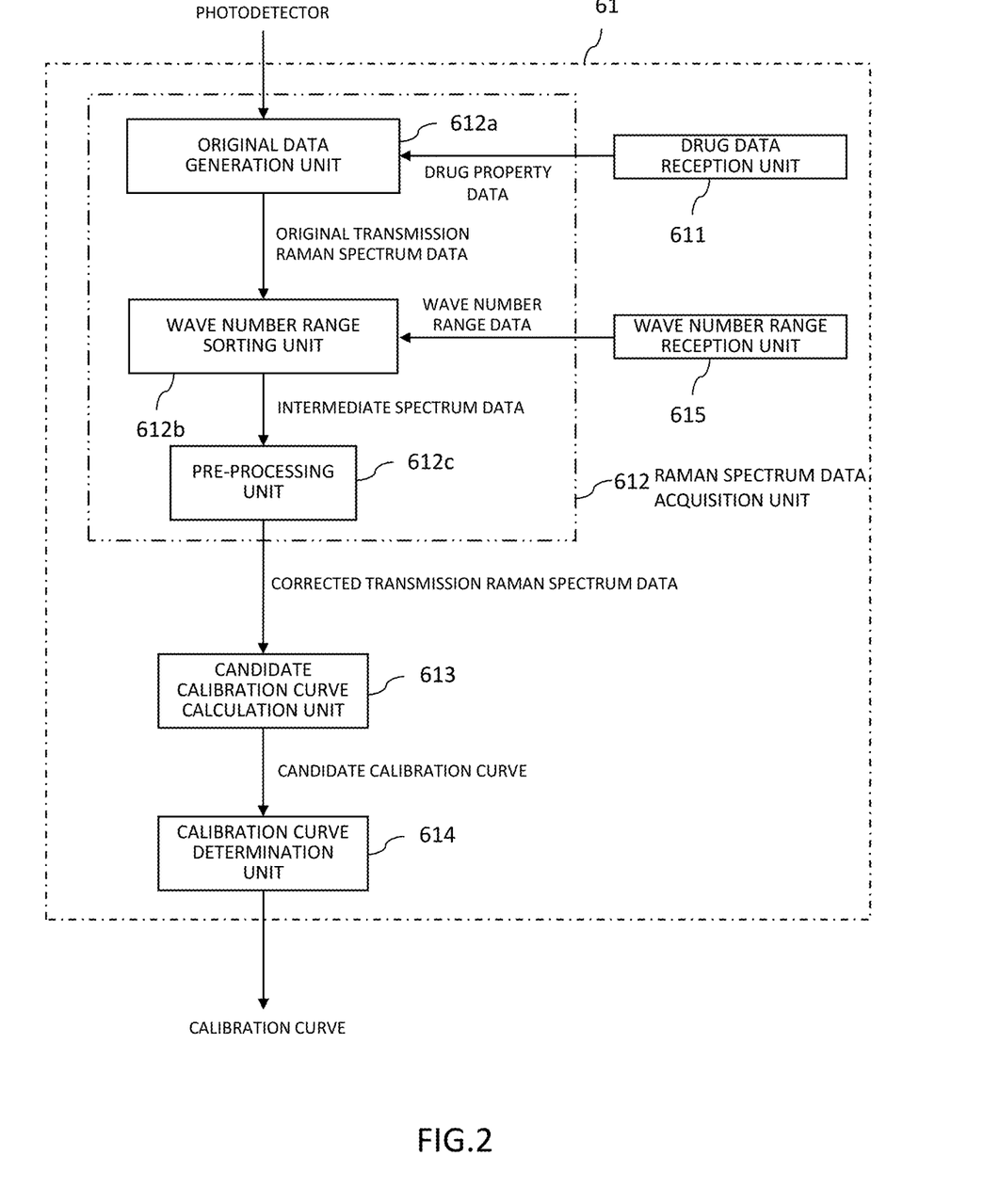
FIG. 2 is a functional block diagram of an information processing unit in the same embodiment.

Next, since a specific feature of this embodiment resides in the calibration curve setting unit 61, it will be described in detail.

As shown in FIG. 2, the calibration curve setting unit 61 includes: a drug data reception unit 611; a Raman spectrum data acquisition unit 612; a candidate calibration curve calculation unit 613; a calibration curve determination unit 614; a wave number range reception unit 615; and the like.

The drug data reception unit 611 receives property data of known, drugs that are a plurality of drugs used for setting the calibration curve by an operator's input operation or via communications from other devices. Note here that the property data is data relating to a specific component contained in each known drug or the concentration of the specific component thereof, and the like.

The Raman spectrum data acquisition unit 612 includes: an original data generation unit 612a, a wave number range sorting unit 612b, and a pre-processing unit 612c. The original data generation unit 612a receives an output signal of the photodetector and generates an original transmission Raman spectrum data which is direct transmission. Raman spectrum data obtained from the known drug. The wave number range sorting unit 612b generates intermediate spectrum data, which is spectrum data of a plurality of different wave number ranges, including wave number components corresponding to the specific components, from the original transmission Raman spectrum data. The pre-processing unit 612c applies a predetermined preprocessing calculation to each of the intermediate spectrum data and generates the corrected transmission Raman spectrum data for each wave number range and for each known drug.

Note here that the wave number range is the wave number (Raman shift $cm^{-1}$) width of the spectrum.

The candidate calibration curve calculation unit 613 calculates respective candidate calibration curves which are candidates of a calibration curve used for quantitatively determining the concentration of the specific component from the data of the plurality of corrected transmission Raman spectra in each wave number range.

The calibration curve determination unit 614 extracts a candidate calibration curve having the smallest residual among the respective candidate calibration curves and determines it as a calibration curve used for quantifying the concentration of the specific component.

The wave number range reception unit 615 receives data (wave number range data) indicating the above-mentioned plurality of wave number ranges by an operator's input operation or via communications from other devices.

Next, regarding the drug analyzer 100 configured as described above, an example of the operation of setting the calibration curve, including the operation procedure of the operator, will be described in detail.

First, in setting the calibration curve, the operator prepares a plurality (in this case, M pieces) of known drugs of which concentrations of components (specific components) to be measured are known and different from each other.

Next, the operator sequentially places the known drugs in the drug holder 3, and each time of placing, the operator inputs the concentrations of the specific components of the known drugs W placed in the drug holder, and each time of inputting, for example, a predetermined laser irradiation start button shown on a display is clicked.

Then, the drug data reception unit 611 receives the input concentration data and stores the data in a predetermined area of the memory. Meanwhile, the known drug W in the drug holder 3 is irradiated with the laser light emitted from the light source 1 and the transmission Raman light generated from the known drug W is introduced into the photodetector 5.

The original data generation unit 612a receives the output signal of the photodetector 5, and generates original transmission Raman spectrum data that is data of a direct transmission Raman spectrum obtained from the known drug W. The original transmission Raman spectrum data is linked to the concentration data of the drug and stored in a predetermined area of the memory.

Figure 3:
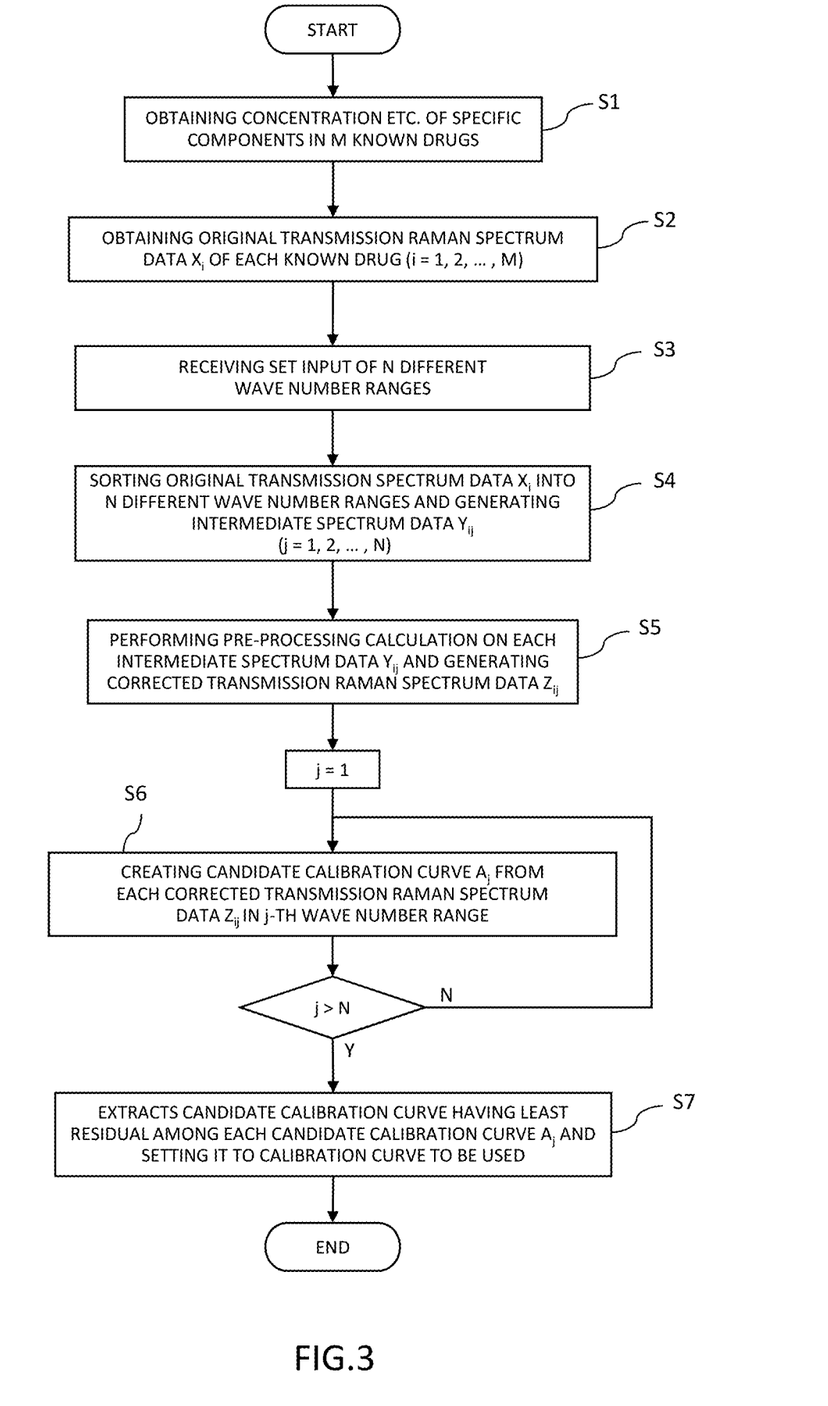
FIG. 3 is a flowchart showing an example of an operation of the drug analyzer in the same embodiment.

Thus, regarding all of the M known drugs, the concentration data of the specific components and the original transmission Raman spectrum data are obtained (see FIG. 3: step S1, step S2).

Next, the wave number range sorting unit 612b generates intermediate spectrum data from the M pieces of original transmission Raman spectrum data, respectively. Here, the intermediate spectrum data is spectrum data of a plurality (in this case, N) of different wave number ranges including the wave number components corresponding to the specific components. Therefore, M×N pieces of intermediate spectrum data is to be generated (see FIG. 3: step S4).

In this case, the plurality of wave number ranges can be inputted and set each time by the operator, and the wave number range reception unit 615 receives the wave number range data, i.e., the inputted data (FIG. 3: step 83). The wave number range sorting unit 612b obtains the resultant wave number range data.

Each wave number range necessarily includes any one peak wave number derived from a specific component in the Raman spectrum, and the wave number range is set in a manner of including the narrowest minimum range, one or more intermediate ranges, and the widest maximum range.

Figure 4:
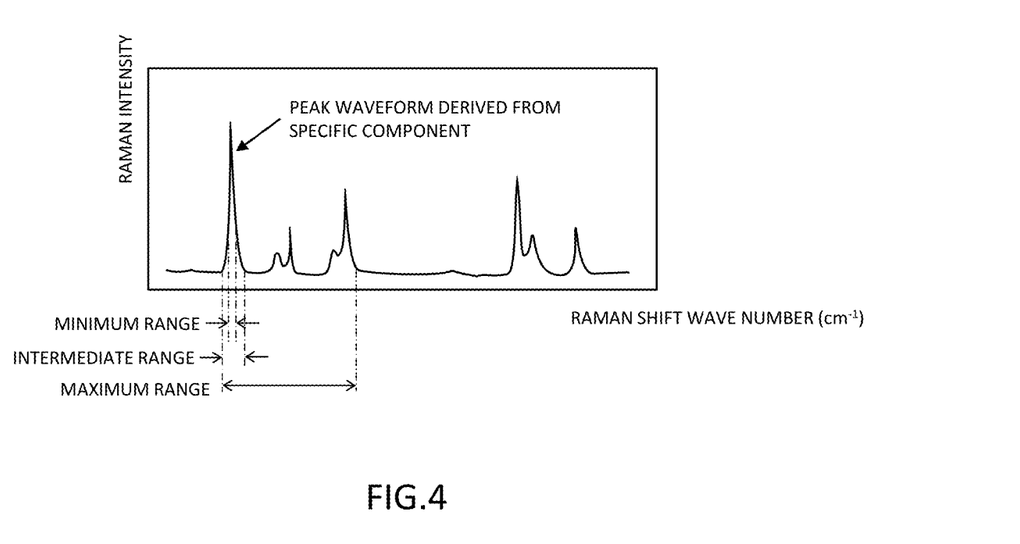
FIG. 4 is an exemplary view showing a specific setting aspect of a plurality of wave number ranges in the same embodiment.

As an example, as shown in FIG. 4, there may be considered an aspect such that, the minimum range is defined as a half width of a peak waveform, the intermediate range is defined as a width including the peak waveform up to about 10% of the peak value, and the maximum range is defined as a width including another peak wave number derived from the specific component.

Figure 5:
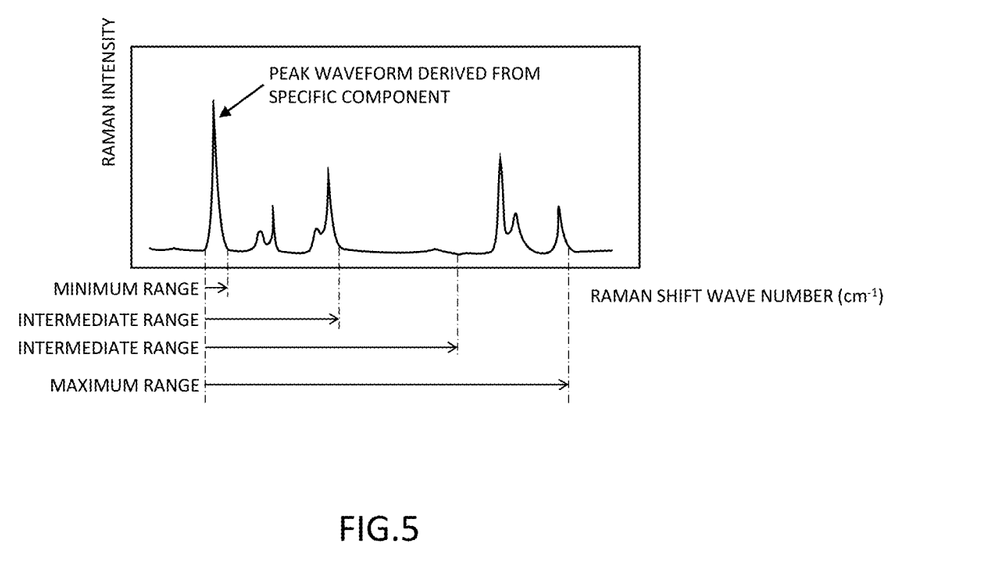
FIG. 5 is an exemplary view showing a specific setting aspect of a plurality of wave number ranges in the same embodiment.

As another example, as shown in FIG. 5, there may be also considered an aspect such that, the minimum wave numbers of all the wave number ranges from the minimum range to the maximum range are the same, and as the range becomes wider, the maximum wave number of the range becomes larger.

In addition, it may be considered that, as the wave number range becomes wider, the minimum wave number is decreased and the maximum wave number is increased, or it may be also considered that, the maximum wave numbers of all wave number ranges from the minimum range to the maximum range are the same and as the range becomes wider, the minimum wave number of the range is decreased.

Note that, each of the wave number ranges may be stored in advance in a predetermined area of the memory without providing the wave number range reception unit 615.

Next, the pre-processing unit 612c performs a predetermined pre-processing calculation on each of the intermediate spectrum data and generates corrected transmission Raman spectrum data which is spectrum data for each of the wave number ranges and for each of the known drugs. The corrected transmission Raman spectrum data generated is M×N pieces (see FIG. 3: step S5). In this case, at least a smoothing process and a multiple scattering correction (MSC) are performed as the pre-processing operation.

Note here that, the smoothing correction is a correction for reducing a spectral noise of the intermediate spectrum data by smoothing.

Note here that, the multiple scattering correction is a method of correcting additive scattering factor and multiplicative scattering factor due to multiple scattering generated in the spectrum.

Figure 6:
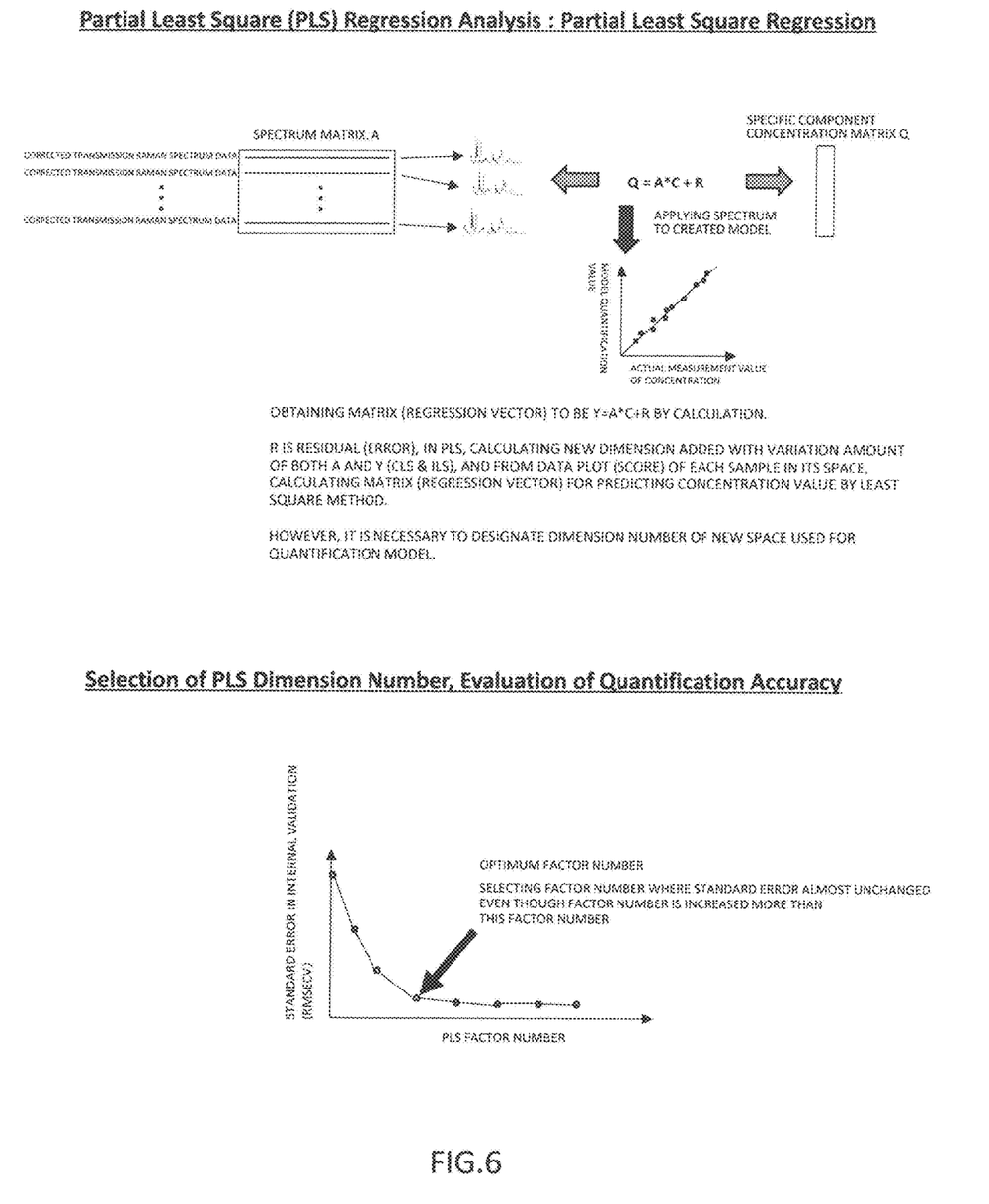
FIG. 6 is an explanatory view of PLS regression analysis in the same embodiment.
Figure 7:
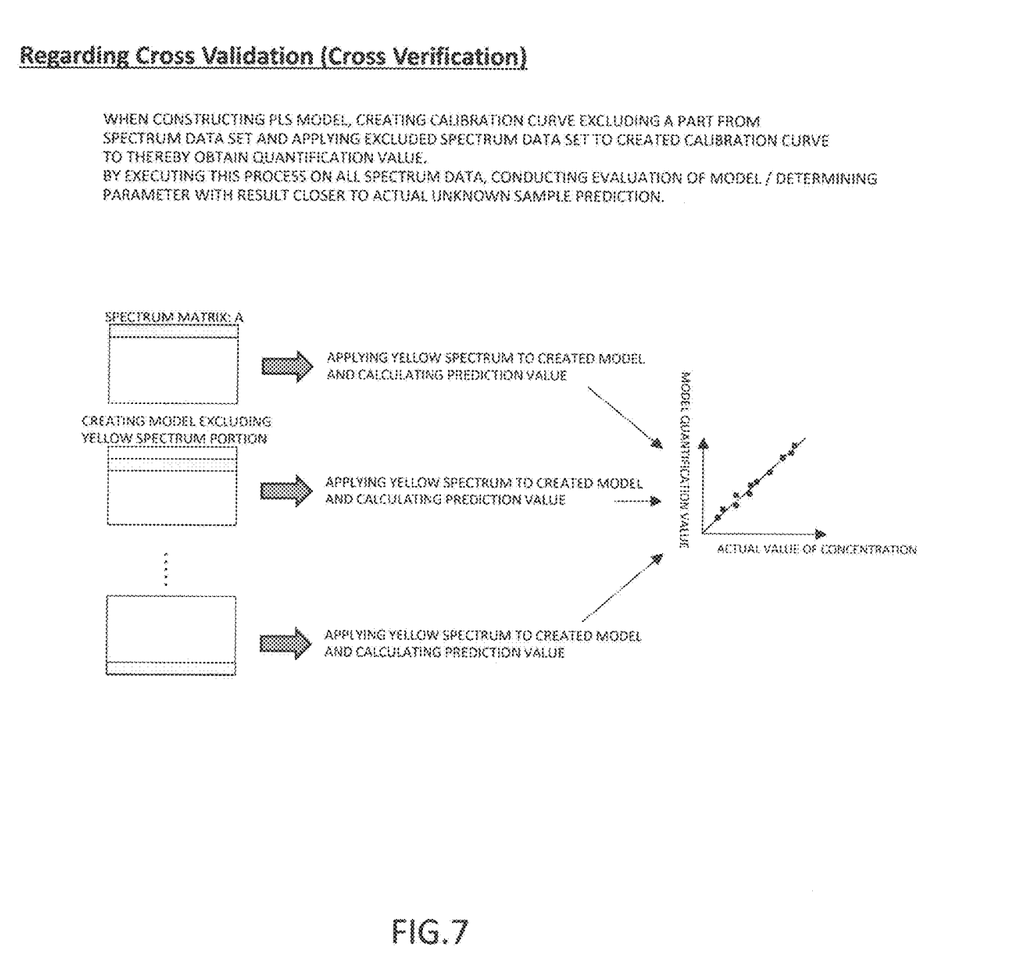
FIG. 7 is an explanatory view of cross validation in the same embodiment.

Next, each of the candidate calibration curves is calculated based on the corrected transmission Raman spectrum data of the same wave number range (see FIG. 3: step S6, up to J=N). For the calculation, partial least squares regression analysis, which is one of multivariate analysis, is used, and cross validation (see FIGS. 6 and 7) is applied to setting of the number of components in the partial least squares regression analysis. By performing this method for all of the wave number ranges; N candidate calibration curves are calculated. At this time, the residual of each candidate calibration curve is also calculated simultaneously. The residual is calculated from an error between each predicted specific component concentration calculated from the candidate calibration curve and actual specific component concentration, and it is such as a root mean square of the error.

In addition, the partial least squares regression analysis and the cross validation will be briefly described here.

In the calculation of the candidate calibration curve, it is necessary to confirm influence on the quantitative accuracy due to the number of dimensions (number of components) of each corrected transmission Raman spectrum data and to reduce the influence almost not to affect. The cross validation is used to determine the influence on the accuracy. In this cross validation, any one of M pieces of corrected transmission Raman spectrum data subtracted by the number of dimensions is used for verification, and M−1 pieces thereof other than the above one is used for training. Then, a calibration curve is generated based on the corrected transmission Raman spectrum data for training, and the calibration curve is applied to the correction transmission Raman spectrum data for verification to thereby calculate a predicted value and obtain a deviation between the predicted value and the actual value (here, known specific component concentration), The above processes are repeated M times while sequentially changing the corrected, transmission Raman spectrum data for verification to obtain M deviations. In the case where the average of these deviations falls within a predetermined allowable range, the number of dimensions is determined to be appropriate.

In addition, another major reason for using the cross validation is because the calibration curve using cross validation is more reliable than the calibration curve obtained by ordinary multivariate analysis.

Finally, the calibration curve determination unit 614 extracts a candidate calibration curve having the least residual among the respective candidate calibration curves, and stores the candidate calibration curve in a calibration curve storage part provided in a predetermined area of the memory (not shown) (FIG. 3: step S) as a calibration curve used for quantifying the concentration of the specific component. At this time, the wave number range corresponding to the calibration curve is also stored as the optimum wave number range in the calibration curve storage part.

According to the present analyzer 100 described above, the candidate calibration curves are calculated respectively based on a plurality of wave number ranges and selects a candidate calibration curve having the least residual as a calibration curve for use in quantification of a specific component. Therefore, the calibration curve can be set using the transmission Raman spectrum close to the optimum wave number range according to ambient conditions such as kinds of specific components and noises and noise. As a result, there can be obtained a calibration curve having higher reliability than in conventional one, and thus the analysis accuracy can be improved. Note that the present invention is not limited to the above embodiment.

The procedure is not limited to the flow chart shown in FIG. 3. For example, the sorting operation to each wave number range may be performed after the pre-processing operation is performed.

The pre-processing procedure may not be necessary in some cases, and only the smoothing processing may be sufficient, or other methods of MSC may be used.

In the present embodiment, although the partial least squares (PLS) regression analysis is used for calculating the respective candidate calibration curves, it is not limited to PLS regression analysis, and other multivariate analysis may be used.

In the present embodiment, although a candidate calibration curve having the least residual is extracted among the candidate calibration curves, it is not limited to this, and a candidate calibration curve having the highest correlation coefficient may be extracted.

Although FIG. 3 shows a flowchart of the M×N operation, it is not limited to this, and, for example, a matrix operation may be used.

In addition, various modifications and combinations may be made without departing from the spirit of the present invention.

REFERENCE SIGNS LIST

100 . . . Drug analyzer
61 . . . Calibration curve setting unit
611 . . . Drug data acceptance unit
612 . . . Raman spectrum data reception unit
613 . . . Candidate calibration curve calculation unit
614 . . . Calibration curve determination unit
615 . . . Wave number range reception unit

The invention claimed is:

1. A calibration curve setting method used at the time of quantitatively analyzing specific components in a drug by a transmission Raman spectrum, the method comprising the steps of:

obtaining, by an operator's input operation, property data of a plurality of known drugs, the property data including concentrations or amounts of the specific components of each of the plurality of known drugs and the concentrations or the amounts are different from each other;

obtaining, from a photodetector of a spectroscope, direct transmission Raman spectrum data of each of the plurality of known drugs;

generating intermediate Raman spectra of different wave number ranges of each of the direct transmission Raman spectrum data of the each of the plurality of known drugs, the different wave number ranges being a different width sections of the direct transmission Raman spectrum data;

calculating candidate calibration curves which are candidates for calibration curves used for the quantitative analysis respectively from the plurality of intermediate Raman spectra for the plurality of the known drugs in each of the different wave number ranges, wherein the candidate calibration curves show relationships between Raman intensity and concentrations of specific components and one of the candidate calibration curves is calculated for each of the different wave number ranges; and using the most probable candidate calibration curve as a calibration curve for the quantitative analysis of the specific components, among the respective candidate calibration curves, wherein the most probable candidate calibration curve corresponds to the candidate calibration curve having the least residual or the candidate curve having the highest correlation coefficient.

2. The calibration curve setting method according to claim 1, wherein each wave number range necessarily includes one peak wave number derived from the specific component in the transmission Raman spectrum data and has a minimum range with a narrowest width, a maximum range with a widest width, and includes one or more intermediate ranges each having an intermediate width between the minimum range and the maximum range.

3. The calibration curve setting method according to claim 1, further comprising a step of applying a predetermined pre-processing calculation to the intermediate Raman spectra and uses the corrected intermediate Raman spectra, in the calculation of the candidate calibration curves, and a step of applying multiple scattering corrections in the pre-processing calculation.

4. The calibration curve setting method according to claim 1, further comprising a step of using multivariate regression analysis which is one of multivariate analysis for calculating the candidate calibration curves and applying cross validation for setting the number of dimensions in the multivariate regression analysis.

5. A drug analyzer for quantitatively analyzing a specific component in a drug by a transmission Raman spectrum, comprising:

an operation receiver for obtaining an operator's input operation directly or via communications from another device, indicating property data of a plurality of known drugs, the property data including concentrations or amounts of the specific components of each of the plurality of known drugs and the concentrations or the amounts are different from each other; and a hardware processor that:

receives the property data from the operation receiver;

obtains direct transmission Raman spectrum data of a plurality of each of the plurality of known drugs from a photodetector of a spectroscope, and generating generates intermediate Raman spectra of different wave number ranges of each of the direct transmission Raman spectrum data of the each of the plurality of known drugs, the different wave number ranges being a different width sections of the direct transmission Raman spectrum data;

calculates candidate calibration curves respectively which are candidates for calibration curves used for the quantitative analysis from the plurality of intermediate Raman spectra for the plurality of known drugs in each of the different wave number ranges, wherein the candidate calibration curves show relationships between Raman intensity and concentrations of specific components and one of the candidate calibration curves is calculated for each of the different wave number ranges; and determines the most probable candidate calibration curve as a calibration curve used for the quantitative analysis of the specific components, among the respective candidate calibration curves, wherein the most probable candidate calibration curve corresponds to the candidate calibration curve having the least residual or the candidate curve having the highest correlation coefficient.

6. A non-transitory recording medium recorded with a program provided on a drug analyzer that quantitatively analyzes a specific component in a drug by a transmission Raman spectrum, causing a hardware processor of the drug analyzer to perform the steps of:

receiving, via an operator's input operation, property data of a plurality of known drugs, the property data including concentrations or amounts of the specific components of each of a plurality of known drugs and the concentrations or the amounts are different from each other;

obtaining direct transmission Raman spectrum data of each of the plurality of known drugs from a photodetector of a spectroscope;

generating intermediate Raman spectra of different wave number ranges of each of the direct transmission Raman spectrum data of the each of the plurality of known drugs, the different wave number ranges being a different width sections of the direct transmission Raman spectrum data;

calculating candidate calibration curves respectively which are candidates of calibration curves used for the quantitative analysis from the plurality of intermediate Raman spectra for the plurality of known drugs in each of the different wave number ranges, wherein the candidate calibration curves show relationships between Raman intensity and concentrations of specific components and one of the candidate calibration curves is calculated for each of the different wave number ranges; and determining the most probable candidate calibration curve as a calibration curve used for the quantitative analysis of the specific components, among the respective candidate calibration curves, wherein the most probable candidate calibration curve corresponds to the candidate calibration curve having the least residual or the candidate curve having the highest correlation coefficient.

* * * * *